United States Patent
Liu et al.

(10) Patent No.: US 6,552,033 B1
(45) Date of Patent: Apr. 22, 2003

(54) IMIDAZO-CONTAINING HETEROCYCLIC COMPOUNDS, THEIR COMPOSITIONS AND USES

(75) Inventors: Song Liu, San Diego, CA (US); David Edward Portlock, Maineville, OH (US); Schwe Fang Pong, West Chester, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/979,571

(22) PCT Filed: May 16, 2000

(86) PCT No.: PCT/US00/13413

§ 371 (c)(1),
(2), (4) Date: Feb. 13, 2002

(87) PCT Pub. No.: WO00/69860

PCT Pub. Date: Nov. 23, 2000

(51) Int. Cl.$^7$ ............... A61K 31/4745; A61K 31/415; C07D 471/04; C07D 487/04; A61P 9/00

(52) U.S. Cl. ............... 514/292; 514/212.05; 514/821; 514/825; 546/84; 540/579

(58) Field of Search ............ 546/84; 514/292, 514/821, 825, 212.05; 540/579

(56) References Cited

U.S. PATENT DOCUMENTS

| | | | |
|---|---|---|---|
| 3,917,610 A | 11/1975 | Takacs et al. | 260/288 |
| 4,143,143 A | 3/1979 | Seiler | 424/258 |
| 6,159,985 A | 12/2000 | Liu et al. | 514/292 |

FOREIGN PATENT DOCUMENTS

| | | |
|---|---|---|
| DE | 135724 | 5/1979 |
| GB | 1438819 A | 7/1976 |
| JP | 49-048663 | 9/1972 |
| JP | 54-048763 | 4/1979 |
| JP | 54-112864 | 9/1979 |
| JP | 07112975 | 5/1995 |
| JP | 08291173 | 11/1996 |
| WO | WO 92/06080 | 4/1992 |
| WO | WO 92/09278 | 6/1992 |
| WO | WO 92/10179 | 6/1992 |
| WO | WO 92/10180 | 6/1992 |
| WO | WO 00/21964 | 9/1999 |
| WO | WO 00/69857 | 5/2000 |

OTHER PUBLICATIONS

Borchard et al., "The Positive Inotropic, Antiarrhythmic and Na+, K+ −ATPase Inhibitory Effects of the Isoquinoline Derivative, BIIA", *Naunyn–Schmiedeberg's Arch. Pharmacol., 312* (1980) pp. 187–192. (Chemical Abstract attached).

Hala et al., "Electrical and Mechanical Activity of the Myocardium as Affected by CH–101, an Antiarrhythmic Agent with Preferential Supraventricular Action", *Adv. Pharmacol. Res. Pract., Proc. Congr Hung Pharmacol. Soc.*, (1986), vol. 1, pp 163–7 (Chemical Abstract attached).

Fox et al., "Mechanism of Inhibition of Sodium– and Potassium–Dependent Adenosine Triphosphatase by the Isoquinoline Derivative BIIA: A Specific Interaction With Sodium Activation", *Biochemical Pharmacology, 30* (1981) pp. 611–617.

Zolyomi et al., "Potential Drugs Labelled with $^{14}$C. I. The Synthesis of 3–Benzylamino–5,6–dihydro–8,9–dimethoxy–imidazo[5,1–a]Isoquinoline hydrochloride", *J. of Labelled Compounds and Radiopharmaceuticals, XVIII* (1980) pp. 813–822.

Borchard et al., "Characterization of Antiarrhythmic Drugs by Alternating Current Induced Arrhythmias in Isolated Heart Tissues", *Arch. Int. Pharmacodyn., 256* (1982) pp. 253–268.

Fulop et al., "A 3–Benzilamino–5,6–dihidro–8,9–dimetoxi–imidazo–(5,1–a)–izokinolin–hidroklorid es Intermedierjei Negyszoghullamu Polarografias Vizsgalata", *Magyar Kemiai Folyoirat, 89* (1983) pp. 293–297.

Keenan et al., Imidazole–5–acrylic Acids: Potent Nonpeptide Angiotensin II Receptor Antagonists Designed Using a Novel Peptide Pharmacophore Model *J. Med. Chem.* 1992. vol. 35, No. 21, 3858–3872.

Miyaura et al., The Palladium–Catalyzed Cross–Coupling Reaction of Phenylboronic Acid with Haloarenes in the Presence of Bases, *Synthetic Communications* 1981 11(7). 513–519.

(List continued on next page.)

Primary Examiner—Evelyn Mei Huang
(74) Attorney, Agent, or Firm—Richard S. Echler, Sr.; David V. Upite

(57) ABSTRACT

The subject invention involves compounds having the structure:

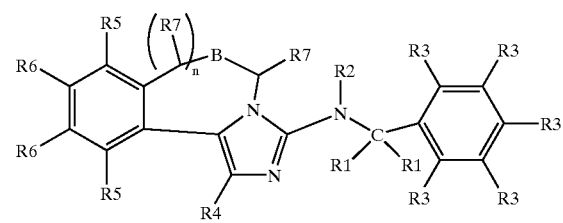

wherein each R1 is independently alkyl, aryl, or heterocycle; each R2–R7 is independently hydrogen or other substituent; B is nil and n is 0–3, or B is ethenyl and n is 0–1; and pharmaceutically acceptable forms thereof. The subject invention also involves pharmaceutical compositions containing such compounds, and methods for treating or preventing diseases or disorders using such compounds.

16 Claims, No Drawings

OTHER PUBLICATIONS

O'Connell et al, Convenient Synthesis of Methyl 1–Methyl–2,4–dibromo–5 imidazolecarboxylate *"Synthesis"*, Oct. 1988, pp. 767–771.

Rapoport et al, J. Organic Chemistry, 1992, vol. 57, p. 1390.

Lipshutz et al, Metalations of Imidazoles (poly) Functionalization and conversions to Imidazolones, Tetrahedron Letters 1988, 29(28) 3411–3414.

Whitten, et al, [2–(Trimethylsilyl) ethoxy] methyl (SEM) as a Novel and Effective Imidazole and fused Aromatic Imidazole Protecing Group, *J of Organic Chemistry* 1986, 51, 1891–1894.

Priimenko et al, Investigations in the Imidazoles Series LXV. Synthesis of 2–Aminoimidazole Derivatives from 2–Haloimidazoles, pp. 1173–1176.

Nishimura, et al *Mechanism of Voges–Proskauer Reaction*, Chemistry Letters, Chemical Society of Japan (1972, pp. 649–652.

Nishimura et al, A Novel Synthesis of 2–(disubstituted amino)–5(4) phenylimidazoles, Dept of Chemistry, School of Hygienic Sciences, Feb. 7, 1975, vol. 12, pp. 47–476.

Choshi et al., Synthesis of Mutagenic Heterocyclic Amines PhIP and DMIP, *J. Org. Chem*, vol. 58 No. 27, 1993, pp. 7952–7954.

IMIDAZO-CONTAINING HETEROCYCLIC COMPOUNDS, THEIR COMPOSITIONS AND USES

This application is the 371 of PCT/US00/13413, filed on May 16, 2000, which claims the benefit of provisional application No. 60/134,822, filed on May 19, 1999.

FIELD OF THE INVENTION

The subject invention relates to novel imidazo-containing heterocyclic compounds, pharmaceutical compositions containing them, and their therapeutic or preventative use in the areas of cardiovascular, oncology, infectious and inflammatory diseases.

BACKGROUND

Certain imidazo-isoquinoline compounds are disclosed in U.S. Pat. No. 3,917,610 issued Nov. 4, 1975; they are reported to have certain cardiovascular activities. One such compound is further reported on in Borchard, Fox, and Greeff, "The Positive Inotropic, Antiarrhythmic and Na$^+$, K$^+$-ATPase Inhibitory Effects of the Isoquinoline Derivative, BIIA", *Achives of Pharmacology*, vol. 312 (1980), pp. 187–192.

SUMMARY OF THE INVENTION

The subject invention includes compounds having the structure:

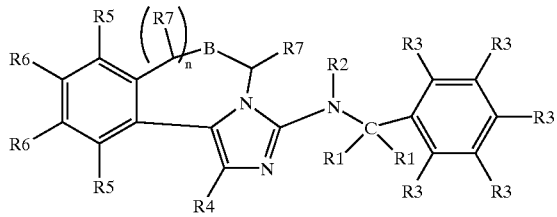

wherein:
(a) each R1 is independently selected from alkyl, aryl, and heterocycle;
(b) R2 is selected from hydrogen, alkyl, alkylacyl, arylacyl, alkylsulfonyl and arylsulfonyl;
(c) each R3 is independently selected from hydrogen, halo, alkyl, aryl, heterocycle, nitro, cyano, and unsubstituted or alkyl- or aryl- or heterocycle-substituted hydroxy, thio, amino, amide, formyl (acyl), carboxy, and carboxamide; two R3's on adjacent carbons may optionally together be alkylene or heteroalkylene, thereby forming a fused ring with the phenyl to which they are attached;
(d) R4 is selected from hydrogen, halo, alkyl, aryl, heterocycle, and carboxy and its alkyl and aryl esters and amides;
(e) each R5 is independently selected from hydrogen, alkyl, and aryl;
(f) each R6 is independently selected from hydrogen, halo, alkyl, aryl, heterocycle, nitro, cyano, and unsubstituted or alkyl- or aryl- or heterocycle-substituted hydroxy, thio, amino, amide, sulfonamide, formyl (acyl), carboxy, and carboxamide; or the two R6's may optionally together be alkylene or heteroalkylene, thereby forming a fused ring with the phenyl to which they are attached;
(g) B is nil or —C(R7)=C(R7)—;
(h) if B is nil, n is an integer from 0 to about 3, otherwise n is from 0 to about 1;
(j) each R7 is independently selected from hydrogen, alkyl and aryl;
and an optical isomer, diestereomer or enantiomer thereof; a pharmaceutically acceptable salt, hydrate, or biohydrolyzable ester, amide or imide thereof.

The subject invention also includes compositions comprising a subject compound and a pharmaceutically-acceptable excipient; and methods for treating or preventing diseases or disorders by administering to a human or lower animal in need thereof, a safe and effective amount of a subject compound.

DETAILED DESCRIPTION OF THE INVENTION

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkylacyl). Preferred linear alkyl have from one to about twenty carbon atoms, more preferably from one to about ten carbon atoms, more preferably still from one to about six carbon atoms, still more preferably from one to about four carbon atoms; most preferred are methyl or ethyl. Preferred cyclic and branched alkyl have from three to about twenty carbon atoms, more preferably from three to about ten carbon atoms, more preferably still from three to about seven carbon atoms, still more preferably from three to about five carbon atoms. Preferred cyclic alkyl have one hydrocarbon ring, but may have two, three, or more, fused hydrocarbon rings. Preferred alkyl are unsaturated with from one to about three double or triple bonds, preferably double bonds; more preferably they are mono-unsaturated with one double bond. Still more preferred alkyl are saturated. Saturated alkyl are referred to herein as "alkanyl". Alkyl unsaturated only with one or more double bonds (no triple bonds) are referred to herein as "alkenyl". Preferred substituents of alkyl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted alkyl are preferred.

As used herein, "heteroatom" means a nitrogen, oxygen, or sulfur atom.

As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryl have from six to about fourteen, preferably to about ten, carbon atoms in the aromatic ring(s), and a total of from about six to about twenty, preferably to about twelve, carbon atoms. Preferred aryl is phenyl or naphthyl; most preferred is phenyl. Preferred substituents of aryl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted aryl are preferred.

As used herein unless specified otherwise, "heterocycle" means a saturated, unsaturated or aromatic cyclic hydrocarbon ring (or fused rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the rings(s); and a total of from three to about twenty carbon plus heteroatoms, more preferably from three to about ten, more preferably still five or six, carbon plus heteroatoms. Preferred heterocycles have one ring, but may have two, three, or more, fused rings. More preferred heterocycle rings include those which are one ring with 5 or 6 carbon plus heteroatoms in the ring with no more than three ring heteroatoms, no more than two of which are O and S. Still more preferred are such 5- or 6-ring atom heterocycles with one or two ring atoms being O or S and the others being C; or with one, two or three ring atoms being N and the others being C. Such preferred 5- or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-ring atom heterocyclic ring. Heterocycles are unsubstituted or substituted. Preferred heterocycle substituents are the same as for alkyl.

COMPOUNDS OF THE INVENTION

The subject invention involves compounds having the following structure:

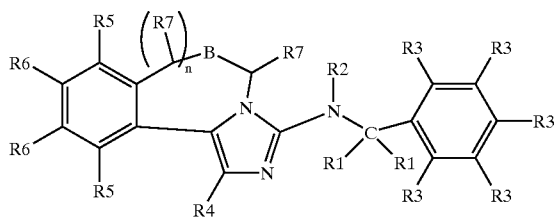

(1)

In structure 1, each R1 is independently selected from alkyl, aryl, and heterocycle. Preferred R1 include linear alkanyl having from 1 to about 6 carbon atoms, linear alkenyl having from 2 to about 6 carbon atoms, and branched and cyclic alkanyl and alkenyl having from 3 to about 6 carbon atoms, such alkenyl preferably having 1 double bond. Such preferred alkanyl and alkenyl are preferably unsubstituted, or substituted with phenyl, heterocycle having 5 or 6 ring atoms, carboxy and its $C_1$–$C_6$ alkyl and phenyl esters, or cyano. More preferably such alkanyl and alkenyl have up to about 5 carbon atoms, more preferably still up to 4 carbon atoms. More preferred R1 are methyl, ethyl and isopropyl. Most preferred R1 is unsubstituted methyl. Also preferred is both R1 being the same moiety.

In structure 1, R2 is selected from hydrogen, alkyl, alkylacyl, arylacyl, alkylsulfonyl, and arylsulfonyl. Preferred R2 is selected from hydrogen; $C_1$–$C_6$ alkyl, such alkyl being saturated or unsaturated with one double bond and unsubstituted or substituted with phenyl; $C_1$–$C_6$ alkylacyl, the alkyl being saturated or unsaturated with one double bond; and phenylacyl. More preferred is the alkyl portions of the aforementioned moieties being $C_1$–$C_4$ and saturated. More preferred still is R2 being methyl. Most preferred R2 is hydrogen.

In structure 1, each R3 is each independently selected from hydrogen, halo, alkyl, aryl, heterocycle, nitro and cyano; also from hydroxy, thio, amino, amide, formyl (acyl), carboxy, and carboxamide which are unsubstituted or substituted, preferably with alkyl or aryl or heterocycle; or two R3 together are alkylene or heteroalkylene attached to adjacent carbon atoms of the phenyl ring, thereby forming a cycloalkyl or aryl or heterocycle ring which is fused to the phenyl ring. Preferred R3 are independently selected from hydrogen, halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl or aryl esters and amides; more preferably from hydrogen, halo, $C_1$–$C_4$ alkyl, thio, $C_1$–$C_4$ alkylthio, $C_1$–$C_4$ mono-or dialkylamino, and $C_1$–$C_4$ alkylacyl. More preferred is for from one to three R3's being halo, the others being hydrogen. Also more preferred is for from one to three R3's being methyl or ethyl, the others being hydrogen. Also preferred is one R3 being dialkylamino, the alkyls having from 1 to about 6 carbon atoms, preferably from about 1 to about 4 carbon atoms, and the others being hydrogen, such R3 preferably being attached to the 4' carbon. More preferred still is for from one to three R3's being independently selected from F, Cl and Br, the others being hydrogen; still more preferred, when two or three R3's are F, Cl or Br, they are the same. Also more preferred, is from one to three R3's being unsubstituted methyl, the others being hydrogen. Also more preferred is one or two R3's being trifluoromethyl, the others being hydrogen.

Also preferred are two R3's which are attached to adjacent carbon atoms of the phenyl ring, together being a saturated or unsaturated alkylene or heteroalkylene having from 1 to about 6 carbon atoms and from 0 to about 3 heteroatoms, thus forming a ring fused to the phenyl, such ring having from about 5 to about 8 ring atoms. Such ring fused to the phenyl preferably has from about 5 to about 6 ring atoms of which from 0 to 2, more preferably 0 or 1, are heteroatoms. Preferred fused rings (including the phenyl to which the R3's are attached) include naphthyl, indolyl, benzimidazoyl, benzofuryl, benzopyranyl. When two R3's form a ring fused with the phenyl, other R3's are preferably H.

In structure 1, R4 is selected from hydrogen, halo, alkyl, aryl, heterocycle, carboxy and its alkyl esters and amides. Preferred R4 is selected from hydrogen, halo, $C_1$–$C_4$ alkyl, phenyl. More preferred R4 is selected from hydrogen and unsubstituted and substituted phenyl; substituents on such phenyl are preferably selected from hydroxy, alkoxy, thio and alkylthio. Most preferred R4 is hydrogen.

In structure 1, each R5 is independently selected from hydrogen, alkyl and aryl. Preferred R5 are selected from hydrogen and alkyl having from 1 to about 4 carbon atoms, especially unsubstituted methyl or ethyl. Most preferred is for both R5 to all be hydrogen.

In structure 1, each R6 is independently selected from hydrogen, halo, alkyl, aryl, heterocycle, cyano and nitro; also from hydroxy, thio, amino, amide, formyl (acyl), carboxy, carboxamide, and sulfonamide which are unsubstituted or substituted, preferably with alkyl or aryl or heterocycle. Preferred R6's are selected from hydrogen, halo, alkyl, aryl, heterocycle, hydroxy, alkoxy, aryloxy, thio, alkylthio, arylthio, amino, alkylamino, arylamino, amide, alkylamide, arylamide, sulfonamide, alkylsulfonamide, arylsulfonamide, formyl, alkylacyl, arylacyl, carboxy and its alkyl and aryl esters and amides; more preferably from hydrogen, halo, hydroxy, $C_1$–$C_4$ alkoxy, thio, $C_1$–$C_4$ alkylthio, $C_1$–$C_4$ alkyl esters and amides of carboxy, and heterocycle having 5 or 6 ring atoms. More preferably one or both R6's are selected such that at least one heteroatom is bonded directly to the phenyl ring. When both R6's have heteroatoms bonded directly to the adjacent carbons of the phenyl ring, the two R6's may together form an alkylene moiety connecting the two heteroatoms, the alkylene moiety preferably having from 1 to about 4, more preferably 1 or 2, carbon atoms. Preferred is that one or both of the R6's are non-hydrogen moieties; more preferred is that both of them are non-hydrogen moieties. More preferred still is that both R6's are alkoxy or both alkylthio; preferably both are the same. Preferred alkyl portions of R6's have from 1 to about 4 carbon atoms, more preferably 1 or 2 carbon atoms; most preferred is methyl. Such alkyl portions are preferably unsubstituted. Such alkyl portions are preferably saturated. Most preferred is that both R6's are methoxy or ethoxy, especially methoxy.

Also preferred are a R5 and a R6, which are attached to adjacent carbon atoms of the phenyl ring, together being a saturated or unsaturated alkylene or heteroalkylene having from 1 to about 6 carbon atoms and from 0 to about 3 heteroatoms, thus forming a ring fused to the phenyl, such ring having from about 5 to about 8 ring atoms. Such ring fused to the phenyl preferably has from about 5 to about 6 ring atoms of which from 0 to 2, more preferably 0 or 1, are heteroatoms. Preferred rings formed by such R5 and R6 include phenyl, furyl, pyrrolyl, dioxanyl, imidazoyl, pyridinyl, pyrrolidinyl, piperidinyl. When such R5 and R6 form a fused ring, the other R5 and R6 are both preferably hydrogen.

In structure 1, B is nil or —C(R7)═C(R7)—. When B is nil, n is an integer from 0 to about 3, preferably 1 or 2. When B is —C(R7)═C(R7)—, n is an integer from 0 to about 1, preferably 0. Preferred B is nil.

In structure 1 and in B, each R7 is independently selected from hydrogen, alkyl, and aryl. Non-hydrogen R7 are preferably phenyl, or alkyl having from 1 to about 4 carbon atoms, preferably 1 or 2 carbon atoms. Such non-hydrogen R7 are preferably unsubstituted. Alkyl R7 are preferably saturated. Preferably no more than one of all the R7's is other than hydrogen. More preferably all R7's are hydrogen.

The subject invention includes optical isomers, diastereomers, and enantiomers of the compounds of structure 1. The subject invention includes pharmaceutically-acceptable salts, hydrates, and biohydrolizable esters, amides and imides of such compounds.

A "pharmaceutically-acceptable salt" is a cationic salt formed at any acidic group (e.g., carboxy group), or an anionic salt formed at any basic group (e.g., amino group) on a compound of structure 1. Many pharmaceutically-acceptable salts are known. Preferred cationic salts include the alkali metal salts, such as sodium and potassium, alkaline earth metal salts, such as magnesium and calcium, and organic salts, such as ammonium. Preferred anionic salts include halides, sulfonates, carboxolates, phosphates, and the like. Salts of addition may provide an optical center where once there was none.

The compounds of the subject invention, and salts thereof, may have one or more chiral centers. The invention includes all optical isomers of the compounds of structure 1 and salts thereof, including diastereomers and enanteomers The subject invention includes and contemplates each optical isomer, diastereomer or enanteomer thereof, in purified form, substantially purified form, and mixtures, including racemic mixtures.

Preferred compounds of the subject invention include those having structure 2:

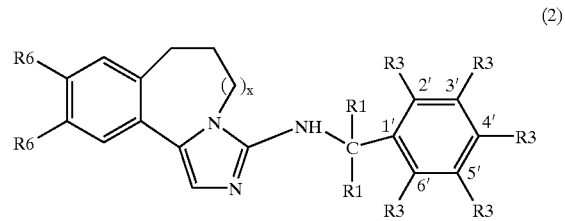

(2)

In structure 2, R1's, R3's and R6's are as described hereinabove, and x is or 1.

In structure 2, each R1 is preferably independantly selected from linear alkanyl having from one to four carbon atoms, linear alkenyl having one double bond and from two to four carbon atoms, branched and cyclic alkanyl having from three to five carbon atoms, and branched and cyclic alkenyl having one double bond and from three to five carbon atoms. Such preferred R1 are unsubstituted or substituted with one phenyl, more preferably are unsubstituted. More preferred R1 are selected from methyl, ethyl, ethenyl, n-propyl, i-propyl, n-propenyl, i-propenyl, s-butyl, cyclopropyl, cyclobutyl, and cyclopentyl. More preferred still R1 are selected from methyl, ethyl, ethenyl, i-propyl, and n-propenyl. Most preferred R1 are methyl. Also preferred is for both R1 to be the same.

In structure 2, one or both of R6, preferably both, are preferably alkylthio or more preferably alkoxy with alkanyl having from one to four carbon atoms. If one R6 is not alkylthio or alkoxy, it is preferably hydrogen. More preferred is both R6 being methoxy or ethoxy; most preferred is both R6 being methoxy.

In structure 2, the R3's are preferably selected from all hydrogen; mono-, di-, or trihalo, preferably selected from fluoro, chloro and bromo, preferably in one or more of the 2', 3', 4' and 5' positions; mono- di-, and trimethyl, preferably in one or more of the 2', 3', 4' and 6' positions; and mono- or di-trifluoromethyl, preferably in one or both of the 3' and 5' positions. Also preferred is one R3 being diakylamino, preferably in the 4' position, the two alkyls preferably being the same and preferably having from 1 to 4 carbon atoms, and the other R3s being hydrogen. More preferred combinations of R3's are selected from 4'-fluoro, 4'-chloro, 4'-bromo, 2',4'-difluoro, 2',4'-dichloro, 2',4'-dibromo, 2',4', 5'-trifluoro, 2',4',5'-trichloro, 3',4'-difluoro, 3',4'-dichloro, dibromo, 4'-methyl, 2',4'-dimethyl, 2',4',6'-trimethyl, 3'-trifluoromethyl, 3',5'-di-trifluoromethyl, and 4'-dibutylamino; in each cased all other R3's being hydrogen. Also preferred R3 combinations are selected from 2',4'-dihalo and 3',4'-dihalo, where one halo is selected from fluoro, chloro, and bromo, and the other halo is a different one of those three; more preferably one of such halo is fluoro, all other R3's having hydrogen. Most preferred R3 combinations are selected from 4'-chloro, 4'-bromo, and 2',4'-dichloro, all other R3's being hydrogen.

Non-limiting examples of compounds of the subject invention include those of structure 2 wherein both R6's are methoxy, and R1's and R3's are as indicated in the following table (R3's not specified are all hydrogen):

| Example | x | R1 | R3 |
|---|---|---|---|
| 1 | 0 | methyl, methyl | hydrogen |
| 2 | 0 | methyl, methyl | 4'-fluoro |
| 3 | 1 | methyl, methyl | 4'-chloro |
| 4 | 0 | methyl, methyl | 4'-bromo |
| 5 | 0 | methyl, methyl | 2',4'-difluoro |
| 6 | 1 | methyl, methyl | 2',4'-dichloro |
| 7 | 0 | methyl, methyl | 2'-fluoro, 4'-chloro |
| 8 | 1 | methyl, methyl | 2'-fluoro, 4'-bromo |
| 9 | 0 | methyl, methyl | 2'-chloro, 4'-fluoro |
| 10 | 1 | methyl, methyl | 2'-bromo, 4'-fluoro |
| 11 | 1 | methyl, methyl | 3',4'-difluoro |
| 12 | 0 | methyl, methyl | 3',4'-dichloro |
| 13 | 0 | methyl, methyl | 3'-fluoro, 4'-chloro |
| 14 | 1 | methyl, methyl | 3'-fluoro, 4'-bromo |
| 15 | 0 | methyl, methyl | 3'-chloro, 4'-fluoro |
| 16 | 1 | methyl, methyl | 3'-bromo, 4'-fluoro |
| 17 | 0 | methyl, methyl | 2',4',5'-trifluoro |
| 18 | 0 | methyl, methyl | 4'-methyl |
| 19 | 1 | methyl, methyl | 2',4'-dimethyl |
| 20 | 0 | methyl, methyl | 3',4'-dimethyl |
| 21 | 1 | methyl, methyl | 2',4',6'-trimethyl |
| 22 | 1 | methyl, methyl | 3'-trifluoromethyl |
| 23 | 0 | methyl, methyl | 3',5'-di-trifluoromethyl |
| 24 | 0 | methyl, methyl | 4'-fluoro, 3'-trifluoromethyl |
| 25 | 1 | ethyl, ethyl | 4'-fluoro |
| 26 | 0 | ethyl, methyl | 4'-chloro |
| 27 | 0 | ethyl, ethyl | 4'-bromo |
| 28 | 1 | ethyl, methyl | 2',4'-dichloro |
| 29 | 1 | ethyl, ethyl | 3'-fluoro, 4'-chloro |
| 30 | 1 | ethenyl, ethenyl | 4'-chloro |
| 31 | 0 | ethenyl, methyl | 2',4'-dichloro |
| 32 | 0 | i-propyl, i-propyl | 4'-fluoro |
| 33 | 0 | i-propyl, methyl | 4'-chloro |
| 34 | 1 | i-propyl, i-propyl | 4'-bromo |
| 35 | 1 | i-propyl, methyl | 2',4'-dichloro |
| 36 | 0 | i-propyl, i-propyl | 3'-fluoro, 4'-chloro |
| 37 | 0 | —CH$_2$—CH=CH$_2$, methyl | 4'-fluoro |
| 38 | 1 | CH$_2$—CH=CH$_2$, CH$_2$—CH=CH$_2$ | 4'-chloro |
| 39 | 1 | —CH$_2$—CH=CH$_2$, ethyl | 2',4'-dichloro |
| 40 | 0 | s-butyl, s-butyl | 4'-chloro |
| 41 | 1 | cyclopentyl, methyl | 4'-chloro |
| 42 | 1 | methyl, methyl | 2',4',5'-trifluoro |
| 43 | 0 | methyl, methyl | 2',3',4'-trifluoro |
| 44 | 0 | ethyl, ethyl | 2',4',5'-trifluoro |
| 45 | 1 | ethyl, ethyl | 2',3',4'-trifluoro |
| 46 | 1 | isopropyl, isopropyl | 2',4',5'-trifluoro |
| 47 | 0 | isopropyl, isopropyl | 2',3',4'-trifluoro |
| 48 | 0 | methyl, methyl | 4'-dibutylamino |
| 49 | 1 | ethyl, ethyl | 4'-dimethylamino |
| 50 | 0 | isopropyl, isopropyl | 4'-diethylamino |

In addition, it is recognized that for purification, administration, and the like, the salts and other derivatives of the above compounds can be used. Thus a pharmaceutically-acceptable salt, hydrate, or biohydrolizable ester, amide or imide thereof is contemplated as part of the subject invention.

METHODS OF MAKING THE COMPOUNDS

In making the compounds of the subject invention, the order of synthetic steps may be varied to increase yield of desired product. The skilled artisan will recognize that the judicious choice of reactants, solvents, and temperatures is important in successful synthesis. The starting materials used in preparing the subject compounds are known, made by known methods, or are commercially available.

It is recognized that the skilled artisan can readily carry out standard manipulations of organic compounds without further direction. These include, but are not limited to, reduction, oxidation, acylation, substitution, etherification, esterification, sulfonation, and the like. Examples of these manipulations are discussed in standard texts.

Procedures for preparing some imidazo-isoquinoline compounds are disclosed in U.S. Pat. No. 3,917,610 issued Nov. 4, 1975, and U.S. Pat. No. 4,143,143 issued on Mar. 6, 1979, both of which are incorporated herein by reference.

The following general schemes can be used for synthesizing compounds of the subject invention. In these schemes, R1, R2, R3, R4, R5, R6, R7, B, and n are as defined hereinabove. Non-conventional symbols and abbreviations for other moieties and chemicals, which may not be clear to the skilled chemist, are defined in the Examples hereinbelow.

General Scheme I

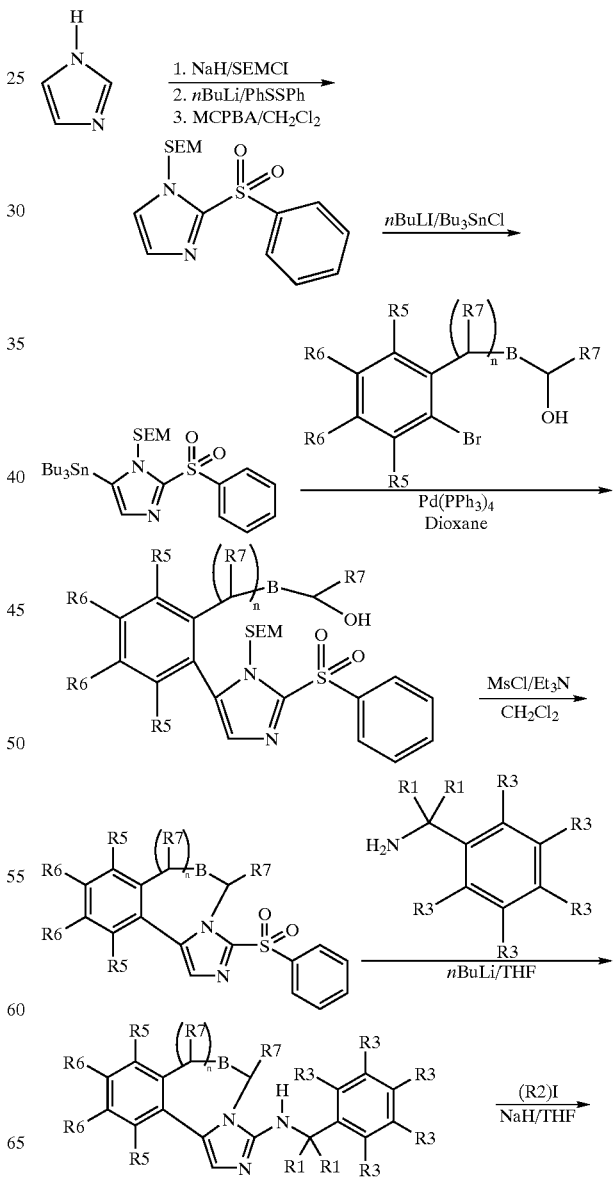

9
-continued

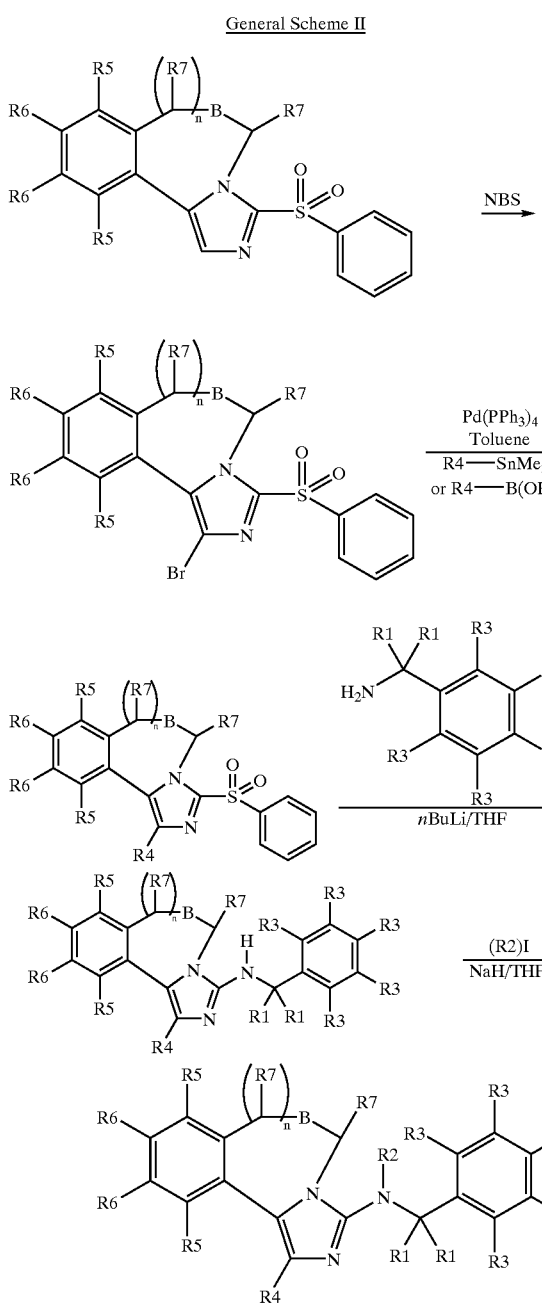

General Scheme II

The following examples provide further information regarding synthesis of the subject invention compounds.

10
PRECURSOR EXAMPLE 1

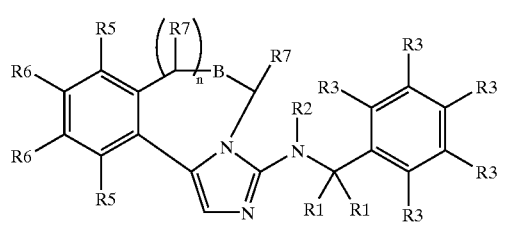

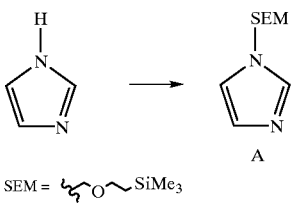

A suspended solution of NaH (6.5 g, 0.162 mol, washed with hexane twice) in anhydrous DMF (300 ml) is cooled in an ice/acetone bath (bath temp. −15° C.). Solid imidazole (10 g, 0.145 mol) is added in small portions and the mixture is stirred at room temperature (r.t.) for 0.5 h; the solution becomes clear. SEM-Cl (25 g, 0.150 mol) is added dropwise by a syringe pump at r.t. over 1 h; NaCl precipitates during the addition. The mixture is stirred at r.t. for about 1 h. Progress of the reaction is monitored by TLC ($CH_2Cl_2$/MeOH, 9:1). $H_2O$ (10 ml) is added with caution to quench the reaction. The solvent is evaporated in vacuo. The residue is dissolved in $Et_2O$ (200 ml) and washed with $H_2O$ (4×50 ml), brine (50 ml), dried ($MgSO_4$), filtered, and evaporated in vacuo to give compound A as an orange liquid.

PRECURSOR EXAMPLE 2

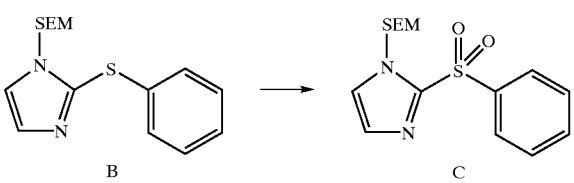

To a solution of SEM-protected imidazole A (1.48 g, 7.50 mmol) in dry THF (75 ml) under argon at −78° C., n-BuLi (1.6 M in hexane) (6 ml, 9.60 mmol) is added dropwise and the mixture is stirred at −78° C. for 30 min. Phenyl disulfide (2.1 g, 9.60 mmol) in THF (2 ml) is then added dropwise. The dry ice/acetone bath is replaced with an ice bath after this addition. The mixture is stirred at 0° C. for 1 h, then at r.t. for 1 h. Progress is monitored by TLC ($CH_2Cl_2$/MeOH, 9:1). $H_2O$ (5 ml) is added to quench the reaction. The solvent is evaporated in vacuo, and the residue is dissolved in $Et_2O$, washed with 5% $NaHCO_3$ (3×20 ml), brine (20 ml), dried ($MgSO_4$), evaporated in vacuo, and purified by chromatography (silica gel, hexane/EtOAc 3:1) to give B as a yellow oil.

PRECURSOR EXAMPLE 3

3-chloroperoxybenzoic acid (MCPBA, 80–85%) (17.03 g, 78.9 mol) is added to a solution of SEM-protected 2-phenylsulfide imidazole B (9.71 g, 31.6 mmol) in anhydrous $CH_2Cl_2$ (160 mL), and the reaction is stirred under argon at room temperature for 15 hours. Progress monitored by TLC (hexane/EtOAc, 3:1). Sodium thiosulfate (3.9 g) is added to remove excess MCPBA. The mixture is filtered. The filtrate is washed with 5% $Na_2CO_3$ (3×150 mL), brine (150 mL), dried ($MgSO_4$), filtered, evaporated in vacuo, and purified by chromatography (silica gel, hexane/EtOAc 3:1) to give C as a light yellow oil.

PRECURSOR EXAMPLE 4

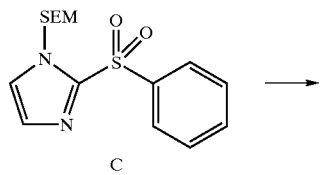

C

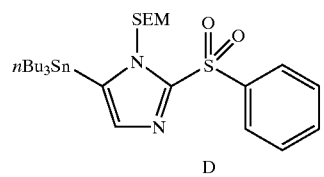

D

To a solution of SEM-protected 2-phenylsulfone imidazole C (8.61 g, 25.4 mmol) in anhydrous THF (250 mL) under argon at −78° C., n-BuLi (1.6 M in hexane) (19.0 mL, 30.0 mmol) is added dropwise by a syringe pump; the solution is stirred at −78° C. for 30 minutes. Tributyltin chloride (6.9 mL, 25.4 mmol) is added dropwise by a syringe pump. The mixture is stirred at room temperature for one hour. Progress is monitored by TLC (hexane/EtOAc, 9:1). $H_2O$ (30 mL) is added to quench the reaction. The solvent is evaporated in vacuo. The residue is dissolved in ether (550 mL) and washed with saturated $NH_4Cl$ (3×150 mL), brine (150 mL), dried ($MgSO_4$), filtered, evaporated in vacuo, and purified by chromatography (silica gel, gradient, hexane (500 mL), hexane/EtOAc, 50:1; hexane/EtOAc, 12:1) to give D as a clear oil.

PRECURSOR EXAMPLE 5

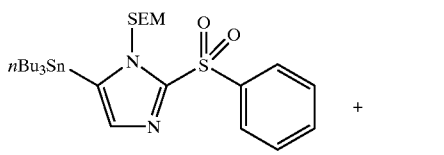

D

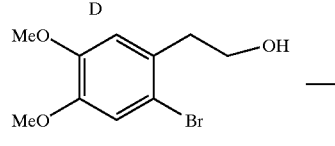

E

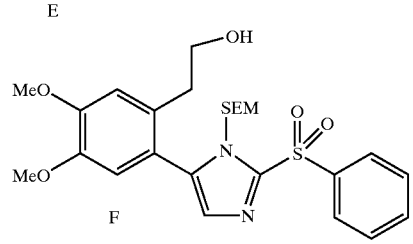

F $Pd(PPh_3)_4$ (0.0177 g, 0.015 mmol) is added to a solution of stannylimidazole D (0.51 g, 0.80 mmol), 4,5-dimethoxy-2-(2-hydroxyethyl)phenyl bromide E (0.33 g, 1.1 mmol), and LiCl (0.087 g, 2.1 mmol) in anhydrous dioxane (4.0 mL) at room temperature. A few crystals (~2 mg) of a radical scavenger, 2,6-di-tert-butyl-4-methylphenol, is added and the reaction is heated to reflux under argon for 5 hours. The reaction is cooled to room temperature and treated with a 1:1 mixture of ether and saturated aqueous KF solution (10 mL) for 15 hours. Progress is monitored by TLC (hexane/EtOAc, 3:1). The mixture is filtered through a pad of Celite with ether rinses. The filtrate is washed with water (3×12 mL), brine (3×12 mL), dried ($MgSO_4$), filtered, evaporated in vacuo, and purified by chromatography (silica gel, hexane/EtOAc, 2:3) to give F as an orange oil.

PRECURSOR EXAMPLE 6

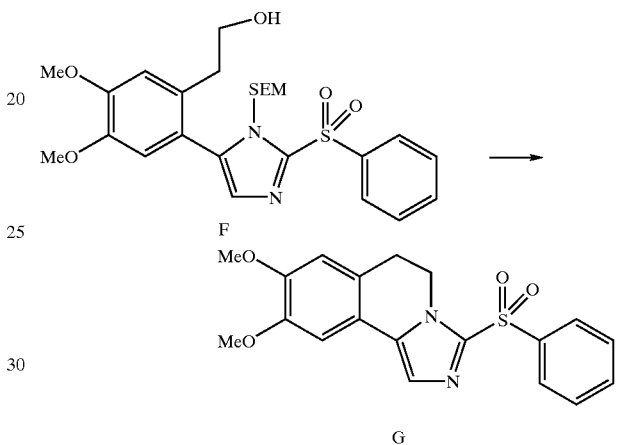

F

G

To a solution of F (2.2 g, 4.24 mmol) and $Et_3N$ (886 μL) in dichloromethane (200 mL) under argon atmosphere at 0° C., methylsulfonyl chloride (MsCl, 492 μL) is added over a peroid of 0.5 h. The reaction is then warmed to room temperature and stirred for 1 h. TLC (EtOAc:Hexane, 1:1) is used to monitor the reaction; it indicates that MsO-ester formation and the SEM-cleavage followed by ring closure occur in one pot. The mixture is diluted with $CH_2Cl_2$ (25 mL), and washed with cold HCl aqueous (0.5N), $NaHCO_3$ aqueous, $H_2O$, brine and dried over $MgSO_4$. Filtration and evaporation of solvent gives a yellow solid. Purification using preparative HPLC (EtOAc:hexane, a gradient from 1:1 to 1:0) provides product G (1.3 g).

Invention Compound Example I

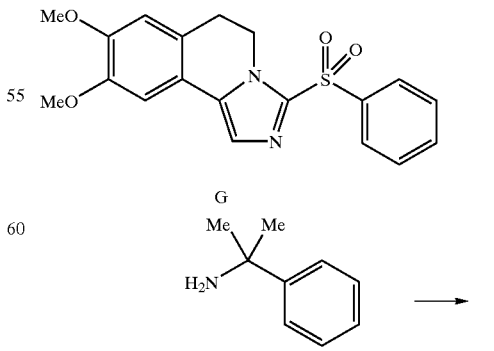

G

H

13 -continued

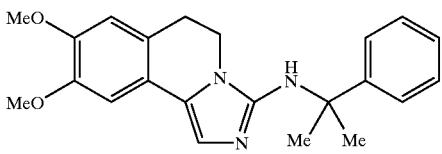

J

In a 25 mL single neck round bottom flask, equipped with a magnetic stir bar, argon inlet, and rubber septum, 1-methyl-1-phenyl-ethylamine (H) (164 mg, 1.2 mmol) in anhydrous THF under argon atmosphere is cooled to 0° C. nBuLi in hexane (0.5 mL, 2.4 M) is added to the solution slowly. The reaction turns light yellow. After stirring for 45 minutes, compound G (150 mg, 0.405 mmol) in THF (1 mL) is added. The solution is warmed to room temperature, and is further heated to reflux for 12 h. TLC ($CH_2Cl_2$:$CH_3OH$, 99:1) indicates completion of the reaction. The solution is quenched with MeOH and evaporated to give a residue which is redissoleved in $CH_2Cl_2$, washed with aqueous $NaHCO_3$ (5%), $H_2O$, brine, and dried over $Na_2SO_4$. The crude product, after filtration and evaporation in high vacuum in order to remove any excess amine H, is purified by chromatography ($CH_2Cl_2$:$CH_3OH$, 99:1) to provide subject invention compound J.

Invention Compound Example II

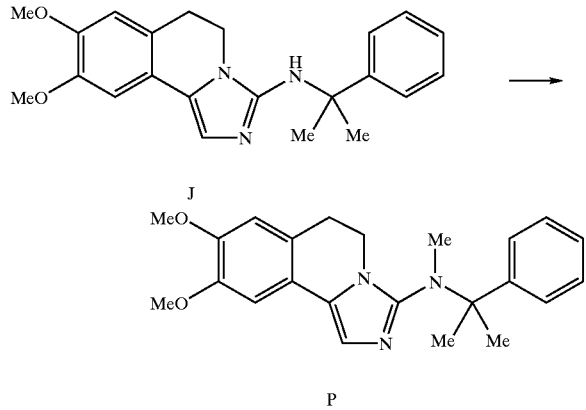

In a 25 mL single neck round bottom flask, compound J (181 mg, 0.5 mmol) in anhydrous THF (10 mL) under argon atmosphere is cooled to 0° C., then NaH (18 mg) pre-washed with hexane is added as a suspension in hexane to the solution. After stirring for 15 minutes, methyl iodide (71 mg, 0.5 mmoll) in THF (0.5 mL) is added. The solution is warmed to room temperature, and further heated to reflux for 2 h to complete the reaction. The solution is quenched with MeOH and evaporated to give a residue which is redissolved in $CH_2Cl_2$, washed with aqueous $NaHCO_3$ (5%), $H_2O$, brine and dried over $Na_2SO_4$. The crude product is purified by chromatography ($CH_2Cl_2$:$CH_3OH$ from 99:1 to 95:5) to provide subject invention compound P.

14

PRECURSOR EXAMPLE 7

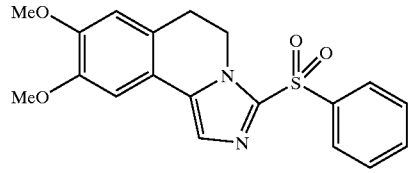

G

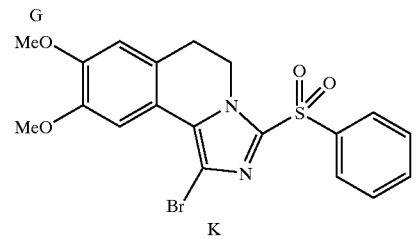

K

N-bromosuccinimide (NBS) solid (98 mg, 0.26 mmol) is added to a solution of compound G (0.5 mmol) in 15 mL of $CCl_4$. Radical initiator benzoyl peroxide (2 mol %) is subsequently added. The flask is placed into a 90° C. oil bath. After 10 min stirring, the reaction is complete. Filtration of the mixture through a celite pad, and evaporation of the filtrate gives a residue. Purification by chromatography (EtOAc:hexane, 1:3 to 1:1) affords compound K.

PRECURSOR EXAMPLE 8

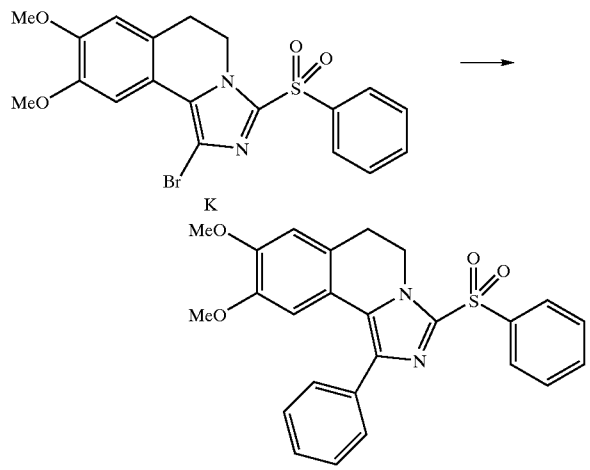

To a solution of K (0.22 mmol) and $Pd(PPh_3)_4$ (13 mg, 0.056 mmol) in 7 mL of anhydrous toluene are added phenyltributyltin (0.26 mmol) and a few crystals (~2 mg) of 2,6-di-tert-butyl-4-methylphenol. The reaction mixture is allowed to reflux at 110° C. under nitrogen for 6 hours to complete the reaction. The reaction mixture is allowed to cool, and is then diluted with 1–2 mL of ethyl acetate (EtOAc). The resultant mixture is washed with water, then brine, extracted with $CH_2Cl_2$, dried over $Na_2SO_4$, and filtered. The filtrate is treated with 3 mL of 30% aqueous KF at room temperature for 2 h. The solid is filtered off. The filtrate is diluted with $CH_2Cl_2$ and washed with water, 30% aqueous $NH_4OH$ (3×), brine, extracted with EtOAc, dried ($Na_2SO_4$), and concentrated in vacuo to yield crude product. Chromatography purification (silica gel, EtOAc:hexane, 1:1 to 1:0) yields compound L.

Subject Invention Example III

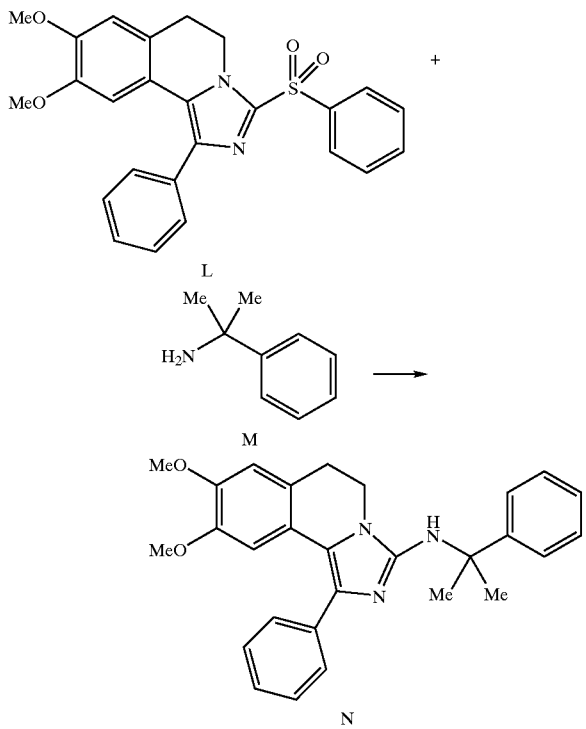

In a 25 mL single neck round bottom flask, equipped with a magnetic stir bar, argon inlet, and rubber septum, (1-methyl-1-phenyl-ethylamine) (M) (1.2 mmol) in anhydrous THF under argon atmosphere is cooled to 0° C. nBuLi in hexane (0.5 mL, 2.4 M) is added slowly to the solution. The reaction turns light yellow. After stirring for 45 minutes, compound L (180 mg, 0.405 mmol) in THF (1 mL) is added. The solution is warmed to room temperature, and is further heated to reflux for 12 h to complete the reaction. The solution is quenched with MeOH and evaporated to give a residue which is redissolved in $CH_2Cl_2$, washed with aqueous $NaHCO_3$ (5%), $H_2O$, brine and dried over $Na_2SO_4$. The crude product, after filtration and evaporation in high vacuum in order to remove excess amine M, is purified by chromatography to provide subject invention compound N.

COMPOSITIONS OF THE INVENTION

A composition of the subject invention comprises:
  a) a safe and effective amount of a compound of the invention; and
  b) a pharmaceutically-acceptable excipient.

Typically, such composition comprises several excipients. It may also optionally comprise other active compounds which do not substantially interfere with the activity of the subject invention compound.

The compositions of the subject invention may be in any of a variety of forms, suitable (for example) for oral, rectal, topical or parenteral administration. Compositions of the subject invention are preferably provided in unit dosage form. As used herein, a "unit dosage form" is a composition containing an amount of a subject compound that is suitable for administration to a human or lower animal subject, in a single dose, according to good medical practice.

As used herein, a "safe and effective amount" of a subject compound is an amount large enough to significantly induce a positive modification in the symptoms and/or condition to be treated in a host, but small enough to avoid serious adverse side effects in the host (such as toxicity, irritation, or allergic response), commensurate with a reasonable benefit/risk ratio. The safe and effective amount will vary with such factors as the particular condition being treated, the age and physical condition of the patient, the duration of treatment, the nature of concurrent therapy (if any), the specific dosage form to be used, and the dosage regimen employed.

The term "pharmaceutically-acceptable excipient", as used herein, includes physiologically inert, pharmacologically inactive substances which are compatible with the physical and chemical characteristics of the subject invention compound used, and which are of sufficiently high purity and sufficiently low toxicity to be suitable for administration to a human or lower animal. The term "compatible", as used herein, means that the excipients of the subject composition are capable of being commingled with the subject invention compound, and with each other in a manner such that there is no interaction which would substantially reduce the pharmaceutical efficacy of the compound, under ordinary use situations.

Depending upon the particular route of administration desired, a variety of pharmaceutically-acceptable excipients well-known in the art may be used. Excipients include, but are not limited to, polymers, resins, plasticizers, fillers, binders, lubricants, glidants, disintegrants, solvents, co-solvents, buffer systems, surfactants, preservatives, sweetening agents, flavoring agents, and dyes or pigments. The amount of excipients employed in conjunction with the subject compound is sufficient to provide a practical quantity of material for administration per unit dose of the subject compound.

Some examples of substances which can serve as pharmaceutically-acceptable excipients are sugars, such as lactose, dextrose, glucose and sucrose; starches, such as cornstarch and potato starch; cellulose and its derivatives, such as methylcellulose, sodium carboxymethylcellulose, ethylcellulose, hydroxypropylcellulose and cellulose acetate; polymers, such as povidone and carbomers; powdered tragacanth; gums, such as xanthan, guar and acacia; malt; solid lubricants, such as stearic acid, magnesium stearate, and talc; inorganic fillers, such as calcium phosphates and calcium sulfate; disintigrants, such as sodium starch glycolate, crospovidone, croscarmelose sodium, and microcrystalline cellulose; encapsulating and coating materials, such as gelatins, waxes, and cellulose derivatives; vegetable oils, such as peanut oil, cottonseed oil, sesame oil, olive oil, corn oil and oil of the obroma; polyols such as propylene glycol, glycerin, sorbitol, mannitol, and polyethylene glycol; alginic acid; surfactants such as the Tweens®, alkyl sulfate salts, salts of fatty acids, sucrose esters; ethyl oleate; coloring agents; flavoring agents; tableting agents; stabilizers; antioxidants; preservatives; solvents, such as ethanol, pyrogen-free water; isotonic saline; and buffer solutions, such as phosphoric, tartaric, citric, and acetic acids, and their sodium, potassium, and ammonium salts.

Preferred compositions of the subject invention are oral dosage forms. The term "oral dosage form", as used herein, means any pharmaceutical composition intended to be systemically administered to an individual by delivering the composition via the mouth to the gastrointestinal tract of an individual. Preferred are oral unit dosage forms, such as tablets, coated or non-coated, and capsules, hard or soft gel. Subject oral unit dosage form compositions comprise preferably at least about 4 mg, more preferably at least about 20 mg, more preferably still at least about 100 mg, and preferably at most about 1000 mg, more preferably at most about 500 mg, more preferably still at most about 250 mg, of a subject compound. Subject oral dosage form compositions comprise preferably at least about 1%, more preferably at least about 10%, and preferably at most about 70%, more preferably at most about 40%, of a subject compound; and comprise preferably at least about 30%, more preferably at least about 60%, and preferably at most about 99%, more preferably at most about 90%, pharmaceutically-acceptable excipients.

Parenteral dosage forms are also preferred subject invention compositions. The term "parenteral dosage form", as used herein, means any pharmaceutical composition intended to be systemically administered to a human or lower animal via delivery of a solution or emulsion containing the active ingredient, by puncturing the skin of the individual, in order to deliver the solution or emulsion to the circulatory system of the individual either by intravenous, intramuscular, intraperitoneal or subcutaneous injection. Subject parenteral unit dosage form compositions comprise preferably at least about 1 mg, more preferably at least about 6 mg, more preferably still at least about 30 mg, and preferably at most about 400 mg, more preferably at most about 100 mg, more preferably still at most about 40 mg, of a subject compound. Subject parenteral dosage form compositions comprise preferably at least about 1%, more preferably at least about 5%, and preferably at most about 20%, more preferably at most about 10%, of a subject compound; and comprises preferably at least about 80%, more preferably at least about 90%, and preferably at most about 99%, more preferably at most about 95%, pharmaceutically-acceptable excipients. In addition, dosages for injection may be prepared in dried or lyophilized form. Such forms can be reconstituted with water, saline solution, or a buffer solution, depending on the preparation of the dosage form. Such forms may be packaged as individual dosages or multiple dosages for easier handling. Where lyophilized or dried dosages are used, the reconstituted dosage form is preferably isotonic, and at a physiologically compatible pH, and comprises the subject compound and excipients in the amounts and percentages indicated previously in this paragraph.

METHODS OF TREATMENT USING THE COMPOUNDS

Subject invention compounds have demonstrated pharmacological activity in processes known to be associated with one or more of cardiovascular activity, inflammatory mechanisms, oncology, and regulation of protein transport from cells. The subject invention includes methods of using the above compounds of the subject invention for therapeutic or preventative treatment of one or more of the following diseases or disorders: congestive heart failure, arrhythmia, hypotension, cardiac reperfusion injury, arteriosclerosis, restenosis, vascular tone, bacterial infection, cancer, Kaposi's sarcoma, psoriasis, migraine, nasal congestion, allergic responses, rheumatoid arthritis, and osteoporosis. Such methods comprise administering to a human or lower animal in need of such treatment or prevention a safe and effective amount of a subject invention compound.

For preferred oral administration of compounds and/or compositions of the subject invention, preferably at least about 0.1 mg/kg, more preferably at least about 0.5 mg/kg, more preferably still at least about 2 mg/kg, and preferably at most about 20 mg/kg, more preferably at most about 5 mg/kg, more preferably still at most about 2 mg/kg, of a subject compound is administered to a human or lower animal, preferably at least about 1 time, more preferably at least about 2 times, and preferably at most about 4 times, more preferably at most about 2 times, daily. Treatment duration using such oral daily dosages is dependent on the disease or disorder being treated; it is preferably at least about 1 day, more preferably at least about 3 days, more preferably still at least 7 days, and preferably at most about 5 years, more preferably at most about 60 days, more preferably still at most about 15 days.

For preferred parenteral administration of compounds and/or compositions of the subject invention, preferably at least about 0.04 mg/kg, more preferably at least about 0.2 mg/kg, more preferably still at least about 1 mg/kg, and preferably at most about 10 mg/kg, more preferably at most about 4 mg/kg, more preferably still at most about 1 mg/kg, of a subject compound is administered to a human or lower animal, preferably at least about 1 time, more preferably at least about 2 times, and preferably at most about 4 times, more preferably at most about 2 times, daily. Treatment duration using such parenteral daily dosages is dependent on the disease or disorder being treated; it is preferably at least about 1 day, more preferably at least about 3 days, more preferably still at least 7 days, and preferably at most about 60 days, more preferably at most about 20 days, more preferably still at most about 5 days.

While particular embodiments of the subject invention have been described, it will be obvious to those skilled in the arts that various changes and modifications of the subject invention can be made without departing from the spirit and scope of the invention. It is intended to cover, in the appended claims, all such modifications that are within the scope of this invention.

What is claimed is:

1. A compound, enatiomer, diasteriomer or pharmaceutically acceptable salt thereof, said compound having the formula:

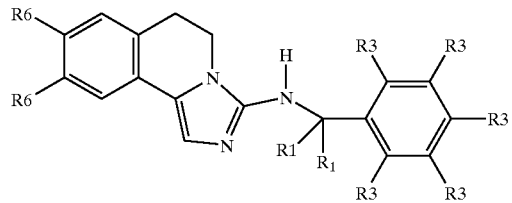

wherein each R1 is independently methyl, ethyl, vinyl, n-propyl, isopropyl, allyl, iso-propenyl, sec-butyl, cyclopropyl, cyclobutyl, or cyclopentyl; each R3 is independently hydrogen, fluoro, chloro, bromo, methyl, trifluoromethyl, dimethylamino, diethylamino, or dibutylamino, each R6 is independently hydrogen, alkylthio, or alkoxy.

2. A compound according to claim 1 wherein each R1 is methyl.

3. A compound according to claim 2, wherein R3 units are selected to form phenyl units selected from the group consisting of phenyl, 4-fluorophenyl, 4-chlorophenyl, 4-bromophenyl, 2,4-difluorophenyl, 2,4-dichlorophenyl, 2-fluoro-4-chlorophenyl, 2-fluoro-4-bromophenyl, 2-chloro-4-fluorophenyl, 2-bromo-4-fluorophenyl, 3,4-difluorophenyl, 3,4-dichlorophenyl, 3-fluoro-4-chlorophenyl, 3-fluoro-4-bromophenyl, 2,4,5-trifluorophenyl, 4-methylphenyl, 2,4-dimethylphenyl, 3,4-dimethylphenyl, 2,4,6-trimethylphenyl, 3-trifluoromethylphenyl, 3,5-bis(trifluoromethyl)phenyl, and 4-fluoro-3-trifluoromethylphenyl.

4. A compound according to claim 1 wherein one R1 is methyl and one R1 is ethyl.

5. A compound according to claim 4 wherein R3 units are selected to form phenyl units selected from the group consisting of phenyl, 4-fluorophenyl, 4-chlorophenyl, 4-bromophenyl, 2,4-difluorophenyl, 2,4-dichlorophenyl, 2-fluoro-4-chlorophenyl, 2-fluoro-4-bromophenyl, 2-chloro-4-fluorophenyl, 2-bromo-4-fluorophenyl, 3,4-difluorophenyl, 3,4-dichlorophenyl, 3-fluoro-4-chlorophenyl, 3-fluoro-4-bromophenyl, 2,4,5-trifluorophenyl, 4-methylphenyl, 2,4-dimethylphenyl, 3,4-dimethylphenyl, 2,4,6-trimethylphenyl, 3-trifluoromethylphenyl, 3,5-bis(trifluoromethyl)phenyl, and 4-fluoro-3-trifluoromethylphenyl.

6. A compound according to claim 1 wherein one R1 is methyl and one R1 is isopropyl.

7. A compound according to claim 6 wherein R3 units are selected to form phenyl units selected from the group consisting of phenyl, 4-fluorophenyl, 4-chlorophenyl, 4-bromophenyl, 2,4-difluorophenyl, 2,4-dichlorophenyl, 2-fluoro-4-chlorophenyl, 2-fluoro-4-bromophenyl, 2-chloro-4-fluorophenyl, 2-bromo-4-fluorophenyl, 3,4-difluorophenyl, 3,4-dichlorophenyl, 3-fluoro-4-chlorophenyl, 3-fluoro-4-bromophenyl, 2,4,5-trifluorophenyl, 4-methylphenyl, 2,4-dimethylphenyl, 3,4-dimethylphenyl, 2,4,6-trimethylphenyl, 3-trifluoromethylphenyl, 3,5-bis(trifluoromethyl)phenyl, and 4-fluoro-3-trifluoromethylphenyl.

8. A compound according to claim 1 wherein each R1 is isopropyl.

9. A compound according to claim 8 wherein R3 units are selected to form phenyl units selected from the group consisting of phenyl, 4-fluorophenyl, 4-chlorophenyl, 4-bromophenyl, 2,4-difluorophenyl, 2,4-dichlorophenyl, 2-fluoro-4-chlorophenyl, 2-fluoro-4-bromophenyl, 2-chloro-4-fluorophenyl, 2-bromo-4-fluorophenyl, 3,4-difluorophenyl, 3,4-dichlorophenyl, 3-fluoro-4-chlorophenyl, 3-fluoro-4-bromophenyl, 2,4,5-trifluorophenyl, 4-methylphenyl, 2,4-dimethylphenyl, 3,4-dimethylphenyl, 2,4,6-trimethylphenyl, 3-trifluoromethylphenyl, 3,5-bis(trifluoromethyl)phenyl, and 4-fluoro-3-trifluoromethylphenyl.

10. A compound according to claim 1 wherein each R6 is methoxy.

11. A compound according to claim 1 wherein each R6 is ethoxy.

12. A compound according to claim 1 having the formula:

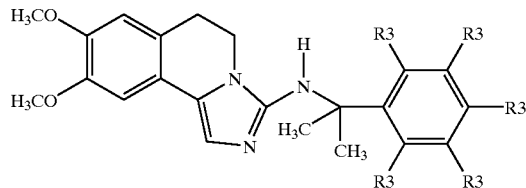

wherein R3 units are selected to form phenyl units selected from the group consisting of phenyl, 4-fluorophenyl, 4-chlorophenyl, 4-bromophenyl, 2,4-difluorophenyl, 2,4-dichlorophenyl, 2-fluoro-4-chlorophenyl, 2-fluoro-4-bromophenyl, 2-chloro-4-fluorophenyl, 2-bromo-4-fluorophenyl, 3,4-difluorophenyl, 3,4-dichlorophenyl, 3-fluoro-4-chlorophenyl, 3-fluoro-4-bromophenyl, 2,4,5-trifluorophenyl, 4-methylphenyl, 2,4-dimethylphenyl, 3,4-dimethylphenyl, 2,4,6-trimethylphenyl, 3-trifluoromethylphenyl, 3,5-bis(trifluoromethyl)phenyl, and 4-fluoro-3-trifluoromethylphenyl.

13. A compound according to claim 1 having the formula:

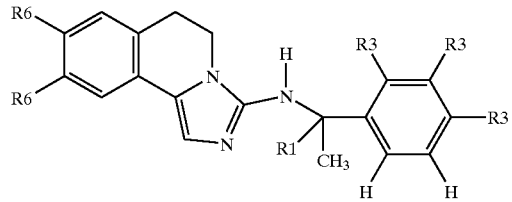

wherein R1 is methyl, ethyl, or iso-propyl; each R3 is independently fluoro, chloro, or bromo; each R6 is independently hydrogen, methoxy, or ethoxy.

14. A composition comprising:

a) one or more compounds having the formula:

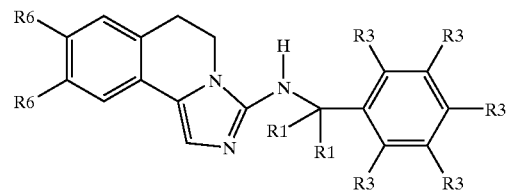

wherein each R1 is independently methyl, ethyl, vinyl, n-propyl, iso-propyl, allyl, isopropenyl, sec-butyl, cyclopropyl, cyclobutyl, or cyclopentyl; each R3 is independently hydrogen, fluoro, chloro, bromo, methyl, trifluoromethyl, dimethylamino, diethylamino, or dibutylamino; each R6 is independently hydrogen, alkylthio, or alkoxy; and b) one or more pharmaceutically acceptable excipients or carriers.

15. A method for treating or preventing congestive heart failure or hypotension, said method comprising the steps of administering to a human or lower animal in need thereof, an effective amount of a compound having the formula:

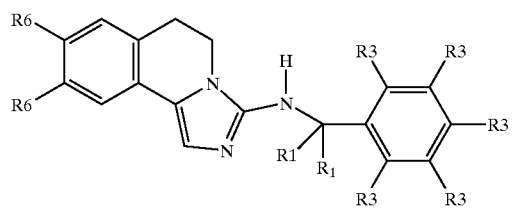

wherein each R1 is independently methyl, ethyl, vinyl, n-propyl, isopropyl, allyl, iso-propenyl, sec-butyl, cyclopropyl, cyclobutyl, or cyclopentyl; each R3 is independently hydrogen, fluoro, chloro, bromo, methyl, trifluoromethyl, dimethylamino, diethylamino, or dibutylamino; each R6 is independently hydrogen, alkylthio, or alkoxy.

16. A method for treating or preventing cardiac arrhythmia or cardiac reperfusion injury caused by cellular protein transport, said method comprising the steps of administering to a human or lower animal in need thereof, an effective amount of a compound having the formula:

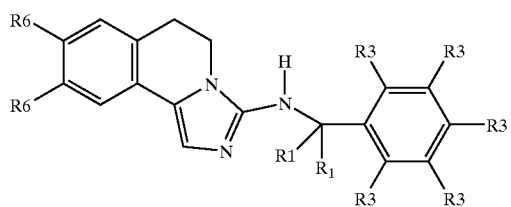
wherein each R1 is independently methyl, ethyl, vinyl, n-propyl, isopropyl, allyl, iso-propenyl, sec-butyl, cyclopropyl, cyclobutyl, or cyclopentyl; each R3 is independently hydrogen, fluoro, chloro, bromo, methyl, trifluoromethyl, dimethylamino, diethylamino, or dibutylamino; each R6 is independently hydrogen, alkylthio, or alkoxy.
* * * * *